US008163881B2

(12) United States Patent
Ober

(10) Patent No.: US 8,163,881 B2
(45) Date of Patent: Apr. 24, 2012

(54) IMMUNOGLOBULIN MOLECULES WITH IMPROVED CHARACTERISTICS

(75) Inventor: E. Sally Ward Ober, Dallas, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 815 days.

(21) Appl. No.: 11/445,475

(22) Filed: May 31, 2006

(65) Prior Publication Data

US 2007/0041907 A1  Feb. 22, 2007

Related U.S. Application Data

(60) Provisional application No. 60/685,934, filed on May 31, 2005.

(51) Int. Cl.
C07K 16/00 (2006.01)
C12P 21/08 (2006.01)
C07K 1/00 (2006.01)

(52) U.S. Cl. ............... 530/387.1; 530/387.3; 530/388.1; 530/388.22

(58) Field of Classification Search .................. None
See application file for complete search history.

(56) References Cited

U.S. PATENT DOCUMENTS

| 6,277,375 | B1 | 8/2001 | Ward | 424/133.1 |
|---|---|---|---|---|
| 7,083,784 | B2 * | 8/2006 | Dall'Acqua et al. | 424/130.1 |
| 7,183,387 | B1 * | 2/2007 | Presta | 530/387.3 |
| 7,670,600 | B2 * | 3/2010 | Dall'Acqua et al. | 424/130.1 |

FOREIGN PATENT DOCUMENTS

| WO | WO 02/060919 | 8/2002 |
|---|---|---|
| WO | WO 2004/035752 | 4/2004 |

OTHER PUBLICATIONS

Rudikoff et al. Proc Natl Acad Sci USA 1982 vol. 79 p. 1979-83.*
Roopenian et al. The Journal of Immunology 2003; 170:3528-3533.*
Burmeister et al., "Crystal structure at 2.2 A resolution of the MHC-related neonatal Fc receptor," Nature, 336-343, 1994.
Bitonti et al., "Pulmonary delivery of an erythropoietin Fc fusion protein in non-human primates through an immunoglobulin transport pathway," Proc. Natl. Acad. Sci. USA, 101:9763-9768, 2004.
Burmeister et al., "Crystal structure at 2.2 a resolution of the MHC-related neonatal Fc receptor," Nature, 336-343, 1994.
Dall'Acqua et al., "Increasing the affinity of a human IgG1 for the neonatal Fc receptor: biological consequences," J. Immunol., 169:5171-5180, 2002.
Dall'Acqua et al., "Properties of Human IgGls Engineered for Enhanced Binding to the Neonatal Fc Receptor (FcRn)," J. Biol. Chem., 281:23514-23524, 2006.
Deisenhofer, "Crystallographic Refinement and Atomic Models of Human Fc Fragments and its Complex with Fragment B and Protein A from Staphylococcus aureus at 2.9- and 2.8-A Resolution," Biochemistry, 20:2361-2370, 1981.

Dickinson et al., "Bidirectional FcRn-dependent IgG transport in a polarized human intestinal epithelial cell line," J. Clin. Invest., 104:903-911, 1999.
Edelman et al., "The covalent structure of an entire gammaG immunoglobulin molecule," Proc. Natl. Acad. Sci., USA, 63:78-85, 1969.
Firan et al., "The MHC class I-related receptor, FcRn, plays an essential role in the maternofetal transfer of gamma-globulin in humans," Int. Immunol., 13(8):993-1002, 2001.
Ghetie and Ward, "Multiple roles for the major histocompatibility complex class I-related receptor FcRn," Annu. Ref. Immunol., 18:739-766, 2000.
Ghetie and Ward., "FcRn: the MHC class I-related receptor that is more than an IgG transporter," Immunol Today, 18(12):592-598, 1997.
Ghetie et al., "Abnormally short serum half-lives of IgG in beta 2-microglobulin-deficient mice," Eur. J. Immunol., 26(3):690-696, 1996.
Hinton et al., "Engineered human IgG antibodies with longer serum half-lives in primates," J. Biol. Chem., 279:6213-6216, 2004.
Israel et al., "Increased clearance of IgG in mice that lack beta2-microglobulin: possible protective role of FcRn," Immunol., 89:573-578, 1996.
Junghans and Anderson, "The protection receptor for IgG catabolism is the beta2-microglobulin-containing neonatal intestinal transport receptor," Proc. Natl. Acad. Sci. USA, 93(11):5512-5516 , 1996.
Kabat et al., In: Sequences of proteins of immunological interest, U.S. Department of Health and Human Services, 1991 (Title Page and Table of Contents).
Kim et al., "Localization of the site of murine IgG1 molecule that is involved in binding the murine intestinal Fc receptor," Eur. J. Immunol., 24:2429-2434, 1994.
Kim et al., "Mapping the site on human IgG for binding of the MHC class I-related receptor, FcRn," Eur. J. Immunol., 29:2819-2825, 1999.
Kobayashi et al., "FcRn-mediated transcytosis of immunoglobulin G in human renal proximal tubular epithelial cells," Am. J. Physiol. Renal Physiol., 282:F358-F365, 2002.
Martin et al., "Crystal structure at 2.8 A of an FcRn/heterodimeric Fc complex: mechanism of pH-dependent binding," Mol. Cell, 7:867-877, 2001.
McCarthy et al., "Bidirectional transcytosis of IgG by the rat neonatal Fc receptor expressed in a rat kidney cell line: a system to study protein transport across epithelia," J. Cell Sci., 113:1277-1285, 2000.
Medesan et al., "Comparative studies of rat IgG to further delineate the Fc:FcRn interaction site," Eur. J. Immunol., 28:2092-2100, 1998.
Medesan et al., "Delineation of the amino acid residues involved in transcytosis and catabolism of mouse IgG1," J. Immunol., 158(5):2211-2217, 1997.
Ober et al., "Exocytosis of IgG as mediated by the receptor, FcRn: an analysis at the single-molecule level," Proc. Natl. Acad. Sci., USA, 101:11076-11081, 2004.

(Continued)

Primary Examiner — Chun Dahle
(74) Attorney, Agent, or Firm — Fulbright & Jaworski

(57) ABSTRACT

The present invention provides for IgG1 molecules with improved characteristics. In particular, substitution mutations are provided that, in combination, facilitate improved placental transfer, improved serum half-life and improved FcRn binding. Substitution mutations are also provided, that in combination, can be used to block FcRn function and thereby increase the clearance rates of other (endogenous or exogenous) IgGs, block placental transport of IgGs and have increased affinity/reduced pH dependence for FcRn binding.

4 Claims, 6 Drawing Sheets

OTHER PUBLICATIONS

Ober et al., "Visualizing the site and dynamics of IgG salvage by the MHC class I-related receptor, FcRn," *J. Immunol*, 172:2021-2029, 2004.

Popov et al., "The stoichiometry and affinity of the interaction of murine Fc fragments with the MHC class I-related receptor, FcRn," *Mol. Immol*, 33:521-530, 1996.

Raghavan et al., "Analysis of the pH Dependence of the Neonatal Fc Receptor/Immunoglobulin G Interaction Using Antibody and Receptor Variants," *Biochemistry*, 34:14649-14657, 1995.

Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.*, 276:6591-6604, 2001.

Spiekermann et al, "Receptor-mediated immunoglobulin G transport across mucosal barriers in adult life: functional expression of FcRn in the mammalian lung," *J. Exp. Med.*, 196(3):303-310, 2002.

Yoshida et al., "Human Neonatal Fc Receptor Mediates Transport of IgG into Luminal Secretions for Delivery of Antigens to Mucosal Dendritic Cells," *Immunity*, 20:769-783, 2004.

Zhou et al., "Conferring the binding properties of the mouse MHC class I-related receptor, FcRn, onto the human ortholog by sequential rounds of site-directed mutagenesis," *J. Mol. Biol.*, 345, 1071-1081, 2005.

Zhou et al., "Generation of mutated variants of the human form of the MHC class I-related receptor, FcRn, with increased affinity for mouse immunoglobulin G," *J. Mol. Biol.*, 332:901-913, 2003.

Blumberg & Lencer, "Anitbodies in the breakdown lane," *Nature Biotechnology*, 23(10):1232-1234, 2005.

Vaccaro et al., "Engineering the Fc region of immunoglobulin G to modualte in vivo antibody levels," *Nature Biotechnology*, 23 (10):1283-1288, 2005.

\* cited by examiner

IMMUNOGLOBULIN MOLECULES WITH IMPROVED CHARACTERISTICS

This application claims benefit of priority to U.S. Provisional Application Ser. No. 60/685,934, filed May 31, 2005, the entire content of which is hereby incorporated by reference.

This invention was made with government support under grant numbers R01 AI39167 and R01 AI55556 awarded by the National Institutes of Health. The government has certain rights in the invention.

BACKGROUND OF THE INVENTION

1. Field of the Invention

The present invention relates generally to the fields of immunology and molecular biology. More specifically, the invention relates to modified Ig molecules with improved characteristics.

2. Description of the Related Art

Immunoglobulin G (IgG) constitutes the most prevalent immunoglobin class in the serum of man and other mammals. Despite fluctuations in rates of synthesis by B cells, IgGs are maintained at remarkably constant levels in the serum. If IgG homesostasis is disturbed, then pathology due to too high (hypergammaglobunemia) or too low (hypogammaglobunemia) can result. Studies indicate that the major histocompatibility complex (MHC)-class I related receptor, FcRn, is involved in the homeostasis of serum IgGs (Ghetie et al., 1996; Junghans and Anderson, 1996; Israel et al., 1996). This receptor most likely acts as a salvage receptor, and this would be consistent with its known ability to transcytose IgGs in intact form across the neonatal gut (Wallace and Rees, 1980; Rodewald and Kraehenbuhl, 1984) and yolk sac (Roberts et al., 1990; Israel et al., 1995) or placenta (Kristoffersen and Matre, 1996; Simister et al., 1996; Leach et al., 1996; Firan et al., 2001). More recent studies indicate that FcRn is also involved in the transport of IgGs across epithelial and endothelial cell barriers of diverse origin (Antohe et al., 2001; McCarthy et al., 2000; Spiekermann et al., 2002; Dickinson et al., 1999; Kobayashi et al., 2002; Yoshida et al., 2004), and this has relevance to the delivery of IgG to different sites in the body. Thus, the use of protein engineering to modify the interaction site of an IgG with FcRn offers a way of modulating the serum persistence, distribution and transport of that antibody.

The interaction sites of FcRn on mouse IgG1 (mIgG1) and human IgG1 (hIgG1) have been mapped using site-directed mutagenesis of recombinant Fc-hinge fragments, followed by analysis of these fragments both in vivo and in vitro (Kim et al., 1994b; Medesan et al., 1996; Medesan et al., 1997; Kim et al., 1999). From these studies, I253 (EU numbering (Edelman et al., 1969)), H310, H435 and to a lesser extent, H436 (Y436 in hIgG1) play a central role in this interaction. These amino acids are located at the CH2-CH3 domain interface (Deisenhofer, 1981), and the mapping of the functional site to these residues is consistent with the crystallographic structure of rat FcRn complexed with rat Fc (Burmeister et al., 1994b; Martin et al., 2001).

The FcRn interaction site encompasses three spatially close loops comprised of sequences that are distal in the primary amino acid sequence. The central role of Fc histidines in building this site accounts for the marked pH-dependence (binding at pH 6.0, release at pH 7.2-7.4) of the Fc-FcRn interaction (Rodewald and Kraehenbuhl, 1984; Raghavan et al., 1995; Popov et al., 1996), as the pKa of one of the imidazole protons lies in this pH range. This pH dependence is essential for the release of FcRn bound IgG molecules when they come to the cell surface following intracellular recycling or transcytosis (Ghetie and Ward, 2000; Ober et al., 2004a). I253, H310, H435 and to a lesser degree, H436, are highly conserved in IgGs of both human and rodent IgGs (Kabat et al., 1991). This, taken together with the isolation of a human homolog of FcRn (Story et al, 1994), indicate that the molecular mechanisms involved in IgG homeostasis and transport are common to both mouse and man and this has implications for the modulation of pharmacokinetics, distribution and delivery of IgGs to different body sites.

In studies to identify the FcRn interaction site on Fc, mutations of Fc fragments (comprising the Fc and hinge region) have been made that reduce the serum half-lives of the corresponding Fc fragments (Medesan et al., 1997; Kim et al., 1994a; Kim et al., 1999). In addition, Fc fragments or IgGs with increased affinity for binding to FcRn have been engineered (Ghetie et al., 1997; Shields et al., 2001; Hinton et al., 2004) and these molecules have increased serum persistence in mice (Ghetie et al., 1997) or cynomologous monkeys (Hinton et al., 2004).

Immunoglobulin Fc domains are also of great interest for purposes of studying the mechanisms of antibody interactions with further molecules of the immune system. These include, depending on the class of antibody, interactions with complement, and binding to specific receptors on other cells, including macrophages, neutrophils and mast cells. More detailed knowledge of the biology of Fc regions is important in understanding various molecular processes of the immune system, such as phagocytosis, antibody-dependent cell-mediated cytotoxicity and allergic reactions.

The production of a longer-lived Fc fragment or antibody having increased binding to Fc receptors is attractive, since such a fragment or antibody can be used, for example, to tag therapeutic reagents. This allows fewer doses of the agent to be used in therapy and possibly even allows lower doses of the agent to be used through its increased persistence in the bloodstream. Additionally, such molecules would be useful, in and of themselves, for therapy against pathogenic agents, cancer and autoimmune diseases. Such antibodies would also be predicted to be more efficiently transported across the placenta during the third trimester of pregnancy when FcRn is active in the maternal fetal transport of IgGs (Simister, 2003). As such, protective antibodies (e.g., anti-pathogen) could be delivered to the developing fetus.

In addition, there are multiple situations in which increased clearance of IgGs from the circulation would be desirable, e.g., in autoimmune diseases such as systemic lupus erythematosus where circulating autoreactive antibodies cause pathology, and in situations where toxins or drugs are to be cleared rapidly from the body using an antibody as a clearing agent. Increased clearance of an antibody should be achievable by using a molecule, such as an engineered antibody, that binds to FcRn with high affinity and does not dissociate rapidly at near neutral pH (unlike naturally-occurring antibodies). Such antibodies would not be released from cells, but would instead be predicted to remain bound to FcRn and block binding of other, lower affinity IgGs. As a result, FcRn function would be blocked and endogenous or therapeutic IgGs would be directed into the lysosomal pathway for degradation (Ober et al., 2004b). The targeting of such 'blocking' antibodies to FcRn might also be useful in the prevention of transport of pathogenic (e.g., autoreactive) antibodies from mother to fetus during pregnancy.

SUMMARY OF THE INVENTION

Thus, in accordance with the present invention, there is provided an IgG1 molecule comprising Lys433, Phe434 and Tyr436. The IgG1 molecule may further comprise one or more of Tyr252, Thr254 and Glu256, specifically Tyr252, Thr254 or Glu256, Tyr252 and Thr254, Tyr252 and Glu256, Thr254 and Glu256, or Tyr252, Thr254 and Glu256. The IgG1 molecule may be a bivalent Ig, a single chain Ig, an IgG1 heavy chain molecule, a full length heavy chain molecule, or a fragment of a full length heavy chain molecule, such as a peptide of 6 to about 50 residues in length. The IgG1 molecule may bind to a pathogen antigen, such as a virus, bacterium, fungus, or a parasite. The IgG1 molecule may also bind to a toxin or an autoimmune antibody or an anti-transplant antibody.

In another embodiment, there is provided a method of increasing IgG clearance rates in a subject comprising providing to said subject an IgG1 molecule comprising Lys433, Phe434 and Tyr436. The IgG1 molecule may further comprise one or more of Tyr252, Thr254 and Glu256, specifically Tyr252, Thr254 or Glu256, Tyr252 and Thr254, Tyr252 and Glu256, Thr254 and Glu256, or Tyr252, Thr254 and Glu256. The IgG1 molecule may be a bivalent Ig, a single chain Ig, an IgG1 heavy chain molecule, a full length heavy chain molecule, or a fragment of a full length heavy chain molecule, such as a peptide of 6 to about 50 residues in length.

In yet another embodiment, there is provided a method of blocking FcRn function in a subject comprising providing to said subject an IgG1 molecule comprising Lys433, Phe434 and Tyr436. The IgG1 molecule may further comprise one or more of Tyr252, Thr254 and Glu256, specifically Tyr252, Thr254 or Glu256, Tyr252 and Thr254, Tyr252 and Glu256, Thr254 and Glu256, or Tyr252, Thr254 and Glu256. The IgG1 molecule may be a bivalent Ig, a single chain Ig, an IgG1 heavy chain molecule, a full length heavy chain molecule, or a fragment of a full length heavy chain molecule, such as a peptide of 6 to about 50 residues in length.

In still yet another embodiment, there is provided a pharmaceutical composition comprising an IgG1 molecule comprising Lys433, Phe434 and Tyr436 and a pharmaceutically acceptable buffer, carrier, diluent or excipient. The IgG1 molecule may further comprise one or more of Tyr252, Thr254 and Glu256, specifically Tyr252, Thr254 or Glu256, Tyr252 and Thr254, Tyr252 and Glu256, Thr254 and Glu256, or Tyr252, Thr254 and Glu256. The IgG1 molecule may be a bivalent Ig; a single chain Ig, an IgG1 heavy chain molecule, a full length heavy chain molecule, or a fragment of a full length heavy chain molecule, such as a peptide of 6 to about 50 residues in length. The IgG1 molecule may be therapeutic or prophylactic for an autoimmune disorder or infection by a pathogenic agent.

In a further embodiment, there is provided a method of providing an IgG1 to a fetus comprising (a) providing an IgG1 molecule comprising Lys433, Phe434 and Tyr436; and (b) contacting said IgG1 molecule with a subject carrying a fetus, wherein said IgG1 molecule facilitates provision of said IgG1 molecule across said placental membrane to said fetus. The IgG1 molecule may be conjugated to a therapeutic or diagnostic agent. The therapeutic agent may be an antibacterial, anti-viral or anti-toxin. The diagnostic agent may be a fluorescent label, a chemilluminescent label, or a chromophore. The IgG1 molecule may be a bivalent Ig, a single chain Ig, an IgG1 heavy chain molecule, a full length heavy chain molecule, or a fragment of a full length heavy chain molecule, such as a peptide of 6 to about 50 residues in length. The IgG1 molecule may be therapeutic or prophylactic for an autoimmune disorder or infection by a pathogenic agent.

Also provided are methods of blocking FcRn function in a subject by providing to said subject an IgG molecule or IgG fragment thereof comprising a variant Fc region with increased binding affinity and reduced pH dependence for FcRn, which IgG or fragment comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 439 or 447 of the Fc region.

Further provied are methods of blocking FcRn function in a subject by providing to said subject an IgG molecule or IgG fragment comprising a variant Fc region with increased binding affinity and reduced pH dependence for FcRn, which IgG or fragment comprises an amino acid modification at any one or more of amino acid positions 252, 253, 254, 256, 288, 307, 309, 310, 311, 314, 348, 433, 434, 435, or 439 of the Fc region.

In still further embodiments, there are provided methods for increasing the serum half life of an IgG1 in a subject comprising providing to said subject an IgG1 molecule comprising Lys433, Phe434 and Tyr436.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." "About" means plus or minus 5% of the stated value.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1A: Recycling model. FIG. 1B: Transcytotic model, in which IgGs are carried across cells (although transcytosis is shown only in the apical to basolateral direction, it may also occur in the basolateral to apical direction). Both recycling and transcytosis may play a role in regulating serum IgG level, whereas transcytosis is important for FcRn-mediated delivery of IgGs across cellular barriers. IgGs are taken up by fluid phase pinocytosis and enter acidic endosomes, in which they have the opportunity to bind to FcRn. For both models, IgGs not bound to FcRn are destined for lysosomal degradation. FcRn molecules are represented by '-', IgG molecules by 'Y'.

genes. This latter vector, and the vector encoding the wild-type human IgG1 constant region genes were generous gifts of Dr. Jefferson Foote (Foote and Winter, 1992). The plasmids encoding mutated heavy chains were transfected into an NSO cell line (HuLys5; Foote and Winter, 1992) expressing an anti-lysozyme light chain. The HuLys5 cell line was generously provided by Dr. Jefferson Foote. The regions that are targeted for mutagenesis in the current invention are indicated.

Figure 3:
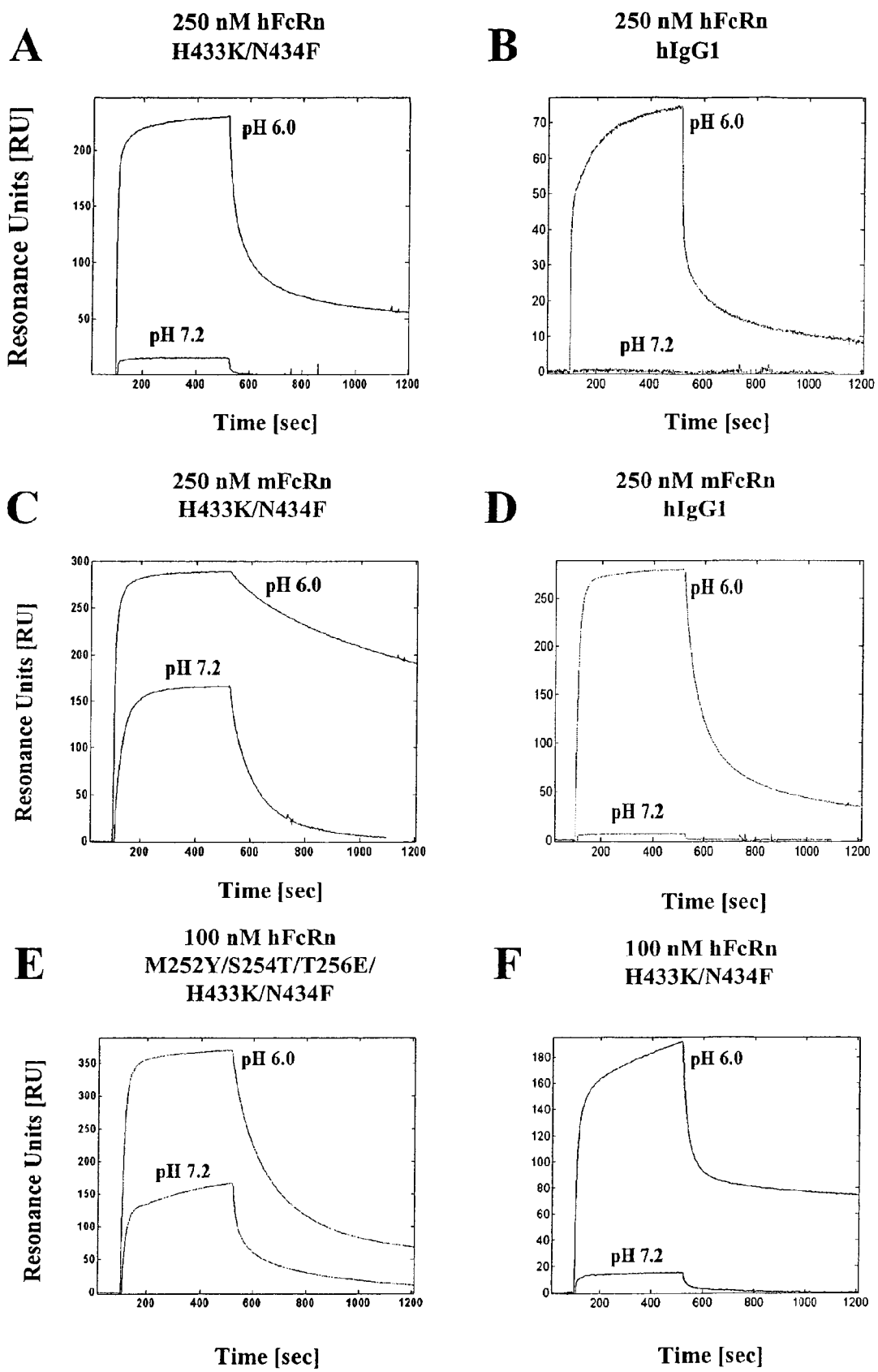

FIGS. 3A-F—The pH dependence of the interactions of human and mouse FcRn (hFcRn and mFcRn, respectively) with wild-type human IgG1 and human IgG1 mutants containing Lys433, Phe434 and Tyr436 (FIGS. 3A-D) and Tyr252, Thr254, Glu256, Lys433 and Phe434 (with wild-type residue Tyr436 retained) (FIGS. 3E,F). Mutants are indicated by the following nomenclature: M252Y=methionine 252 (wild-type residue) mutated to tyrosine, etc. Flow cells of BIAcore sensor chips were coupled with human IgG1 (wild-type or mutant) and hFcRn or mFcRn injected over the surface at the concentrations shown at either pH 6.0 or pH 7.2 in phosphate buffered saline (PBS) plus 0.01% Tween 20. A flow rate of 10 µl/min was used for all experiments. All data shown are reference cell subtracted. Comparison of FIGS. 3A, 3B, 3E and 3F indicates that the addition of Tyr252, Thr254, Glu256 to human IgG1 containing Lys433, Phe434 and Tyr436 results in a human IgG1 variant that binds with less pH dependence to hFcRn (similar results are seen for binding to mFcRn; data not shown). In addition, the mutant containing Lys433, Phe434 and Tyr436 shows less pH dependence for binding to mFcRn than to hFcRn (compare FIGS. 3A and 3C).

Figure 4:
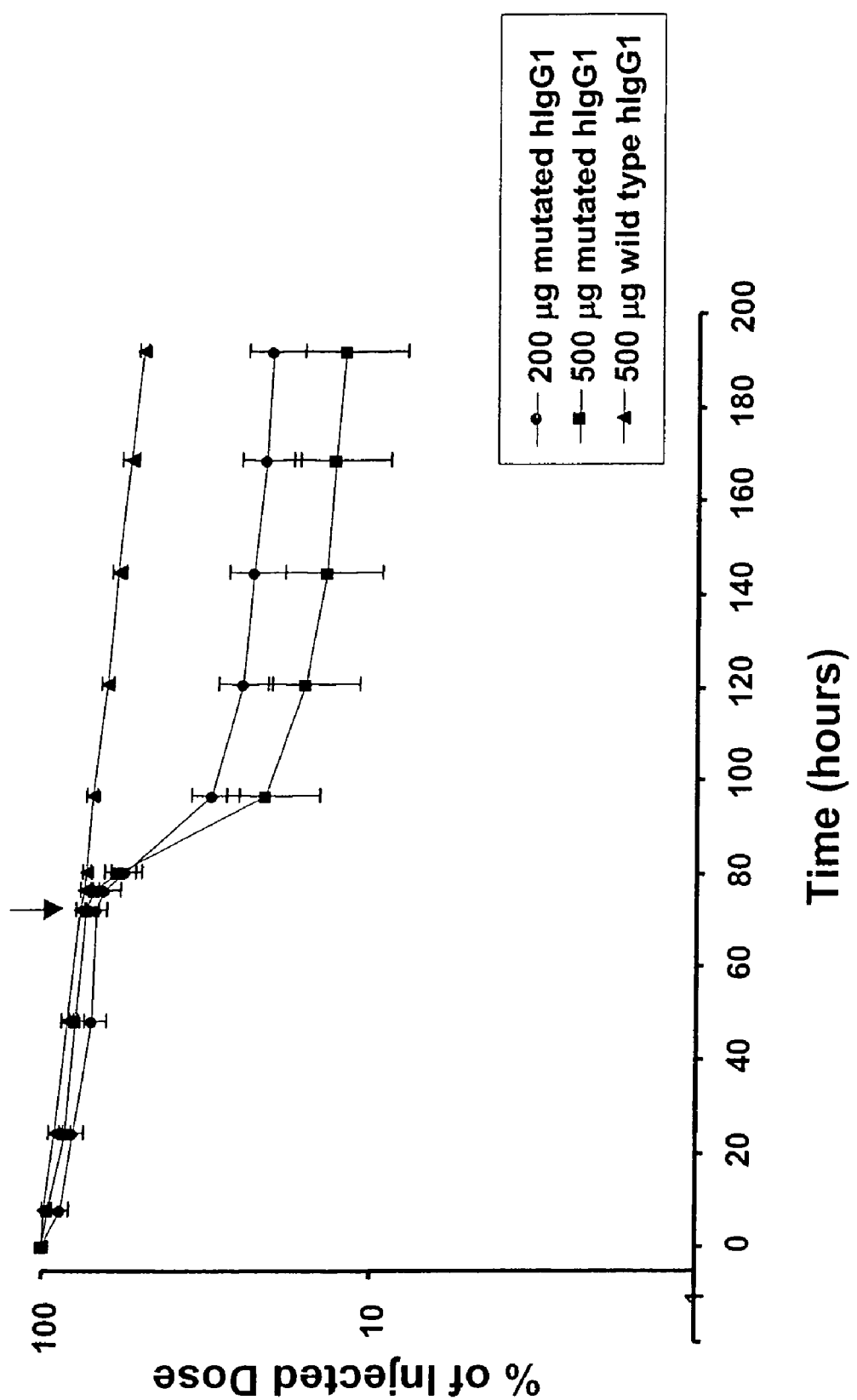

FIG. 4—Enhancement of clearance of injected wild-type human IgG1 (hIgG1) by mutated human IgG1. Swiss mice (six mice/group) were injected with $^{125}$I-labeled wild-type human IgG1 and the persistence of the labeled IgG1 monitored by whole body counting. Three days later (indicated by arrow), mice were injected intravenously with 500 pg wild-type human IgG1 or 500 µg mutated human IgG1 containing Tyr252, Thr254, Glu256, Lys433, Phe434 and Tyr436. Levels of $^{125}$I labeled human IgG1 were determined at the indicated times by whole body counting. The data shown are means of the remaining radioactivity in the different groups of mice. Error bars indicate standard deviations.

Figure 5:
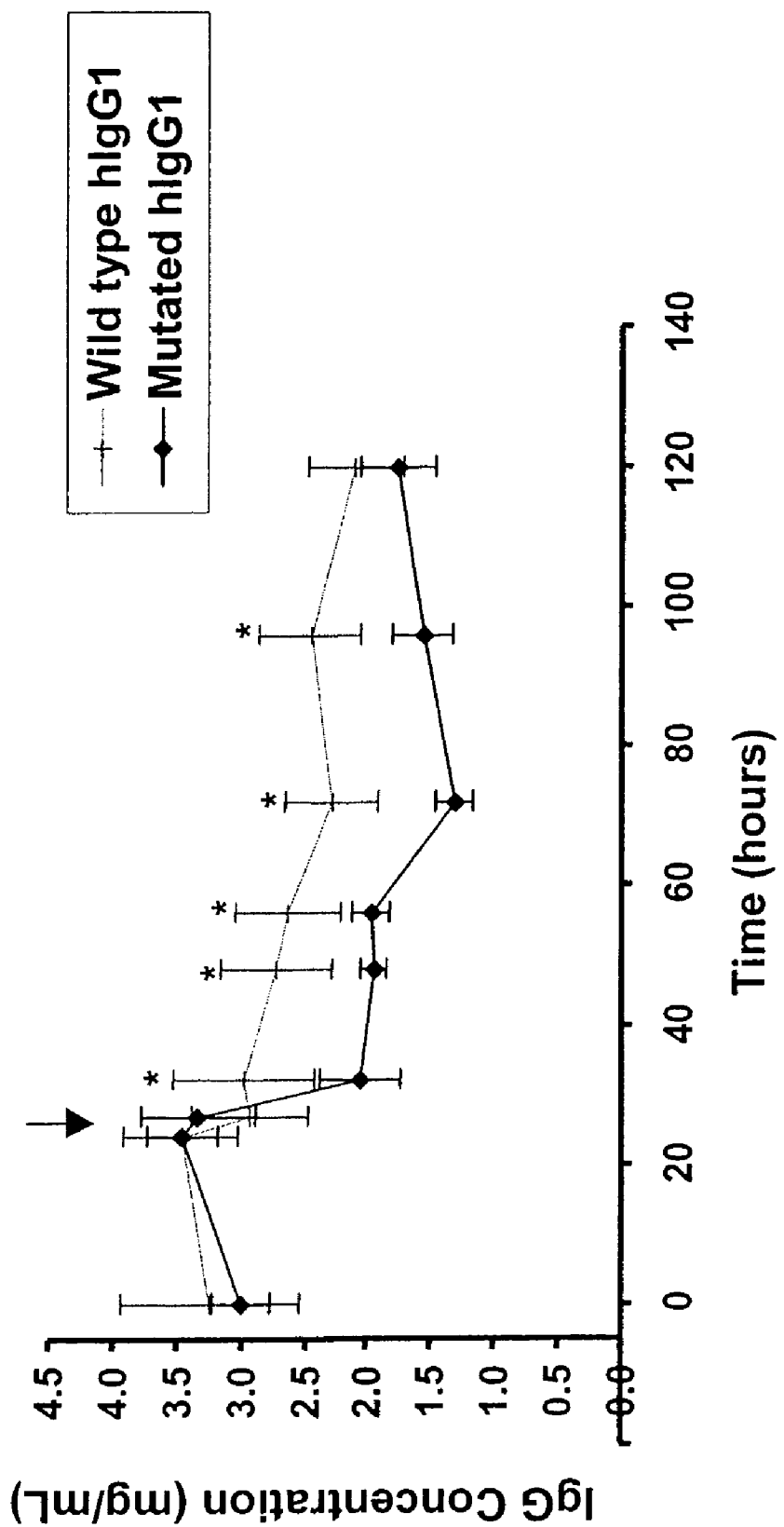

FIG. 5—Enhancement of clearance of endogenous IgGs by mutated human IgG1 containing Tyr252, Thr254, Glu256, Lys433, Phe434 and Tyr436. The serum IgG levels in Swiss Webster mice were quantitated by ELISA. Mice (6 mice/group) were subsequently injected intravenously with 500 µg mutated human IgG1 (hIgG1) containing Tyr252, Thr254, Glu256, Lys433, Phe434 and Tyr436) or 500 µg wild-type human IgG1 and serum IgG levels monitored at the indicated times. The arrow indicates the time of injection of the human IgG1 (wild-type or mutant). Data shown are means of averages of six mice per treatment group with standard deviations indicated by error bars. * indicates that data for these time points are significantly different for each of the two groups, with a p value (Student's t-test) of <0.05.

Figure 6:
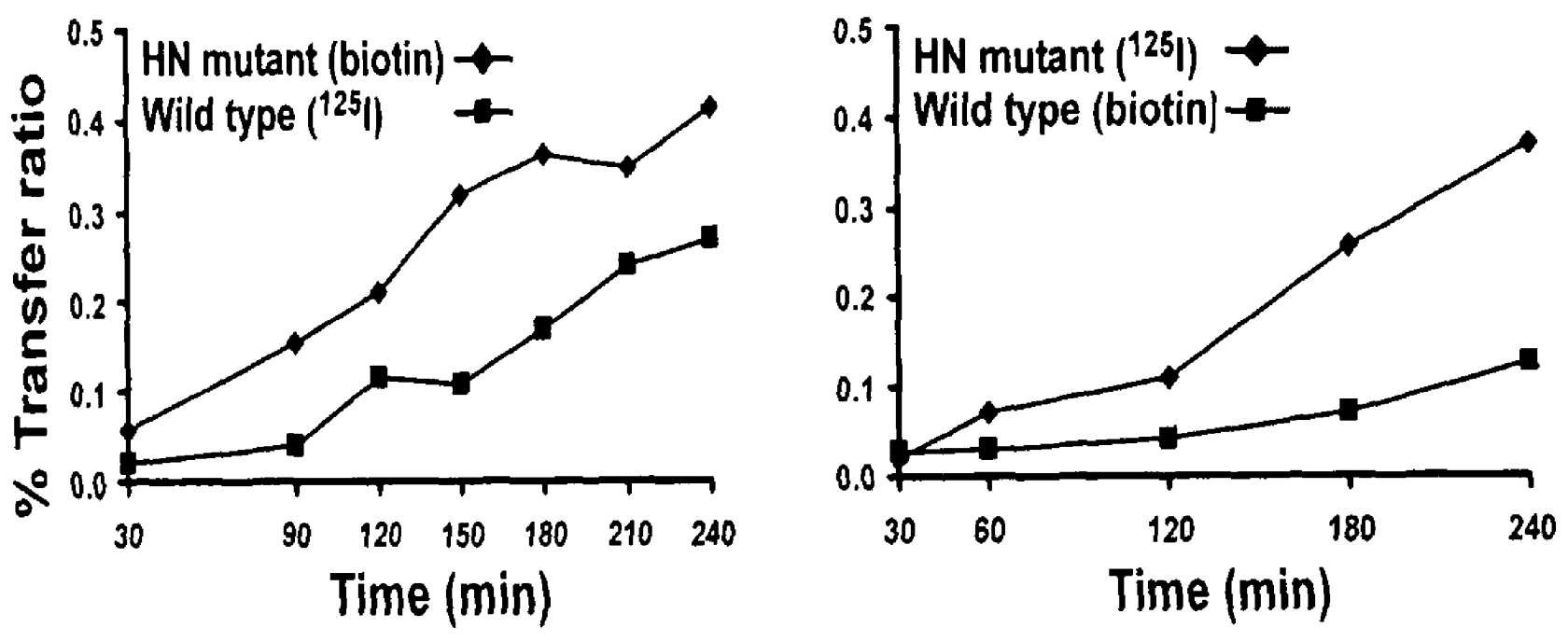

FIG. 6—Analyses of transport of wild-type human IgG1 and a mutated human IgG1 containing Lys433, Phe434 and Tyr436 (His433 to Lys, Asn434 to Phe; 'HN mutant') across the ex vivo perfused placenta. Biotinylated and iodinated IgGs were premixed and added to the maternal compartment. Transport of each IgG into the fetal compartment was assessed from 30 min to 240 min post-addition as described in the Methods.

DETAILED DESCRIPTION OF THE INVENTION

The present invention concerns the cloning and expression of human IgG1 molecules engineered to have improved characteristics, such as improved FcRn binding, increased serum half life and transplacental transfer or transport across other cellular barriers. The invention also concerns the generation of engineered antibodies that have the ability to block FcRn function. More specifically, the invention is exemplified by the production of various mutant IgG1 molecules having a beneficial combination of altered and wild-type residues.

Disclosed herein are recombinant vectors encoding human IgG1 molecules. These DNA constructs and proteins coded thereby are envisioned to be of various uses, such as in the production of immunotherapeutics or other stable recombinant proteins, or in the provision to subjects for therapy.

1. Antibody Constant Domains

FcRn has been isolated from duodenal epithelial brush borders of suckling rates (Rodewald and Kraehenbuhl, 1984; Simister and Rees, 1985) and the corresponding genes cloned for both human and mouse FcRn (Simister and Mostov, 1989a; Simister and Mostov, 1989b; Ahouse et al., 1993). This Fc receptor comprises a heterodimer of two polypeptides of 51 kDa and 14 kDa. Interestingly, the 14 kDa component is β02-microglobulin and the 51 kDa component is homologous to the heavy chain of Class I MHC proteins. The protein can be expressed in high yields in recombinant form and has been analyzed by x-ray crystallography (Burmeister et al., 1994a; Burmeister et al., 1994b; Martin et al., 2001). Importantly, FcRn orthologs have been isolated from multiple species including humans (e.g., Story et al., 1994; Kacskovics et al., 2000), indicating that FcRn is present across mammalian species.

Recombinant Fc molecules, and fragments derived from the murine IgG1 constant regions, can be expressed from host cells. These molecules and fragments can be purified, radiolabeled and used in clearance studies in mice. These regions also may be employed in protein chimeras, or fusion proteins, to produce biologically stable therapeutic agents. This is particularly useful for the production of therapeutic agents which cannot be obtained from other expression systems, such as mammalian cells, due to proteolysis. As such, the Fc domains of the present invention, or portions thereof, are proposed to be useful modules for both the stabilization and delivery of recombinant molecules, including chimeric proteins of therapeutic use.

2. Improving the Characteristics of IgG1S

The maintenance of serum IgG concentrations at a fairly constant level is of importance for effective immunity. Moreover, abnormally high (hypergammaglobulinemia) or low (hypogammaglobulinemia) serum IgG levels result in clinical symptoms. To be effective, the homeostatic mechanism that both senses and regulates serum IgG levels must be able to deal with continuous and variable production of IgG molecules by the B cells of the organism. How such homeostasis is brought about is as yet unclear, and several mechanisms have been proposed to account for the control of IgG levels in the serum (Brambell et al., 1964; Brambell, 1966; Ghetie et al., 1981). Clearly, any model must invoke a feedback system that is both sensitive and responsive to changes in serum IgG levels. In addition, the transport of IgGs across cellular barriers is an important process in mediating protective humoral immunity, and is most likely closely related to the processes that regulate serum IgG levels.

The features of an immunoglobulin molecule that determine stability and other properties in vivo have been the subject of much study. The current model for how IgG levels are regulated in the body is that the Fc receptor, FcRn, binds to IgGs and transports them within and across cells. Binding to FcRn by naturally occurring IgG is pH dependent, with much tighter binding at pH 6.0 than at pH 7.2-7.4 (Raghavan et al., 1995; Popov et al., 1996; Zhou et al., 2003). In most cell types the pH at the cell surface is near neutral and as a result, non-permissive for FcRn-IgG interactions. IgGs are therefore taken into cells by fluid phase pinocytosis rather than receptor mediated uptake. If, following uptake by fluid phase pinocytosis, IgGs do not bind to FcRn then they undergo lysosomal degradation (Ober et al., 2004b). Following recycling or transcytosis by FcRn, IgGs are released by exocytosis at the cell surface (Ober et al., 2004a). Thus, and consistent with the earlier model proposed by Brambell and colleagues prior to the identification of FcRn and the elucidation of the molecular mechanisms of FcRn function (Brambell et al., 1964; Brambell, 1966), the cells that are responsible for IgG breakdown are paradoxically also involved in protection of IgGs against breakdown.

FcRn is expressed at multiple sites throughout the body (e.g., endothelium, epithelium, monocytes, dendritic cells), and therefore serves not only to regulate IgG levels by acting as a salvage receptor (reviewed in Ghetie and Ward, 2000), but also plays a role in transporting IgG across cellular barriers (Antohe et al., 2001; McCarthy et al., 2000; Spiekerman et al., 2002; Dickinson et al., 1999; Kobayashi et al., 2002; Yoshida et al., 2004). Consistent with the idea that FcRn plays a central role in regulating serum IgG levels, IgGs or Fc fragments are cleared rapidly from the circulation of mice that are deficient in functional FcRn expression (Ghetie et al., 1996; Junghans and Anderson, 1996; Israel et al., 1996). Conversely, increasing the affinity of an IgG for FcRn would be predicted to increase its serum half life, and the present inventor has described IgG mutants with improved serum half-life (U.S. Pat. No. 6,277,375; Ghetie et al., 1996). Such antibodies would also be expected to be more efficiently transported across cellular barriers.

Further, IgGs that are engineered to bind with higher affinity and dissociate more slowly than their parent molecules from FcRn should be able to block FcRn function. Such antibodies might therefore have therapeutic uses in situations where it is desirable to reduce the levels of IgG in the body, for example, in diseases where pathogenic antibodies are involved or in the antibody mediated clearance of toxic molecules.

3. Catabolic Site of the IgG Molecule

The site(s) at which IgGs are catabolized and the proteases involved have yet to be characterized. Both liver and gastrointestinal tract have been shown to play a role in the catabolism of IgG (Covell et al., 1986; Hopf et al., 1976; Dobre and Ghetie, 1979) but neither organ, however, has been demonstrated to be the major site of catabolism. Therefore the possibility of diffuse catabolism throughout the body must be considered (Waldmann and Strober, 1969). This is also consistent with the ubiquitous nature of FcRn expression in endothelium and epithelium (reviewed in Ghetie and Ward, 2000). It is possible that such diffuse catabolism could occur in the endothelial system throughout the body since the cells of this system are in close contact with the intravascular pool and IgG constantly traverses the endothelial cells to enter the extravascular space (Ghetie et al., 1996). Consistent with this, recent data support the notion of diffuse catabolism with probable involvement of endothelial cells (Borvak et al., 1999; Ober et al., 2004a, 2004b).

4. Transfer of IgG Across Membranes (Transcytosis)

As part of the present invention, it is contemplated that provision of antibodies in passive immunity will be achieved. In particular, improved transfer across cells and serum persistence of engineered antibodies is contemplated. In another embodiment, blockade of transport of IgGs within (recycling) or across (transcytosis) cells is envisaged by using IgGs that are designed to block FcRn function. A discussion of various transcellular transfer embodiments is provided below.

A. Intestinal Transfer in Newborns

An Fc receptor, now know to be FcRn, was originally implicated in transfer of IgG from the colostrum or milk into the bloodstream of newborn rats and mice (Brambell, 1966; Rodewald, 1976; Kim et al., 1994). Consistent with the concept that FcRn is the transport receptor, maternal IgGs are not delivered to offspring in mice that do not express functional FcRn (Israel et al., 1995). Thus, the available data indicate that IgG transcytosis in rats, mice and humans are carried out by similar receptors and as a consequence share a common mechanism.

The proposed mechanism of trans-intestinal transport is similar to that described above (Section 2), with the exception that the intestinal lumen is at a pH (6.0-6.5) permissive for FcRn-IgG interactions: FcRn on the lumenal side of intestinal epithelial cells binds IgG and the IgG-FcRn complexes are transported across the cell to the basolateral surface where exocytosis occurs into the bloodstream of the newborn rodent. Association of IgG with FcRn as it traffics through the cell is postulated to protect the IgG molecule from lysosomal degradation. The pH of the plasma (7.3) results in release of the bound IgG into the circulation, consistent with the pH dependence of the FcRn-IgG interaction (Raghavan et al., 1995; Popov et al., 1996).

B. Transfer Across Murine Yolk Sac (Maternal-Fetal Transfer)

Murine FcRn is expressed at high levels in both neonatal intestine and yolk sac (Ahouse et al., 1993), and an FcR that is structurally similar to FcRn has also been isolated from rat yolk sac (Roberts et al., 1993). These data strongly suggested that maternal-fetal and intestinal transport are carried out by FcRn, although the cellular location for IgG binding to FcRn appears to differ in the two processes (Roberts et al., 1993). Consistent with the involvement of FcRn, maternal IgGs are not transported to the developing fetus in mice that lack functional FcRn (Israel et al., 1995). In rats, yolk sac FcRn is located in vesicles in the apical and basolateral cytoplasm, and not on the lumenal surface of the yolk sac endodermal cells (Roberts et al., 1993). The difference in location is believed to be necessary because the pH of the lumen surrounding the yolk sac is slightly basic (Roberts et al., 1993), and the affinity of binding of FcRn to IgG is low at this pH (Raghavan et al., 1995; Popov et al., 1996); thus, it has been suggested that maternal IgG is taken up by the yolk sac cells in a non-specific endocytic step and then binds to FcRn in a slightly acidic endosomal compartment. Delivery of IgG into the fetal circulation is then proposed to occur in a similar way to that of intestinal transcytosis (Roberts et al., 1993).

More recent studies demonstrate that for transport of an IgG across the placenta, binding to human FcRn is essential (Firan et al., 2001), implicating FcRn in maternal-fetal transfer in humans. It is therefore expected that maternal transfer of passive immunity to infants will be improved if the affinity of the FcRn-IgG (or Fc) interaction is increased and serum persistence is lengthened. For enhanced serum persistence and maternal-fetal transfer of a therapeutic IgG, it is preferable to endow that IgG with a higher affinity for binding to the Fc receptors such as FcRn that are involved in the processes. As a result, the higher affinity IgGs should be able to out-compete the high concentrations of endogeneous IgGs (about 5 mg/ml in mice and 10 mg/ml in humans). Analogously, blockade of FcRn function using engineered IgGs (or fragments thereof) might be useful in preventing the transfer of deleterious maternal antibodies to the fetus.

C. FcRn-Mediated Transport Across Epithelial Barriers

FcRn was originally identified as the receptor that transports IgGs across the epithelial cells of neonatal intestine, where FcRn is highly expressed. However, more recent studies have shown that FcRn is functionally active in adult epithelial cells of diverse origin such as intestinal, bronchial and kidney epithelium (Spiekerman et al., 2002; Dickinson et al., 1999; Kobayashi et al., 2002; Yoshida et al., 2004). Significantly, FcRn can transport Fc-fusion proteins across bronchial epithelium (Spiekermann et al., 2002; Bitonti et al., 2004), and also plays a role in the delivery of antibody-antigen complexes across the gut (Yoshida et al., 2004). The latter process may play an important role in initiating immune responses against mucosal antigens. FcRn is therefore involved in transporting IgGs (and their bound antigen; Yoshida et al., 2004) to diverse body sites throughout adult life.

The current invention has relevance to the transporting function of FcRn. For example, antibodies with improved binding properties for FcRn might be transported more efficiently across the adult gut or lung, providing a route of delivery for therapeutic IgGs. Alternatively, IgGs that block FcRn function might be useful for the blockade of, for example, bronchial FcRn that might relate to the blockade of allergic responses.

5. FcRn Interaction Site on the IgG Molecule

Of the Ig class (IgA, IgE, IgM, IgD and IgG), the IgG molecule has the longest in vivo half life (Zuckier et al., 1990). The region of the IgG molecule that regulates serum persistence has been known for several decades to reside in the Fc fragment. This work, carried out initially by Spiegelberg and Weigle (1966) and later confirmed by many others (reviewed in Zuckier et al., 1990), indicated that the Fc fragment produced by proteolysis has the same in vivo half life as the complete IgG molecule. Works by Dorrington and colleagues (Dorrington and Painter, 1974; Ellerson et al., 1976; Yasmeen et al., 1976) showed that a CH2 domain fragment produced by trypsin digestion had the same half life as that of the complete IgG molecule. Although both earlier and more recent data suggest that the CH2 domain is involved in the regulation of serum persistence of IgGs, some of these data are not inconsistent with the additional involvement of the CH3 domain (Arend and Webster, 1977; Dima et al., 1983; Mueller et al., 1990; Kim et al., 1994a; Batra et al., 1993). Indeed, other work has indicated that the CH2 domain, and to a lesser extent the CH3 domain, contain sequences that control the serum persistence of IgG molecules (Kim et al., 1994a; Pollock et al., 1990, Kim et al., 1994c). In particular, site-directed mutagenesis has been used to identify amino acid residues in the CH2-CH3 domain interface that are critical for the maintenance of serum IgG1 levels in mice (Kim et al., 1994a; Medesan et al., 1997), and these studies therefore resulted in the precise localization of the FcRn binding site. The residues involved in binding to FcRn are highly conserved in both human and murine IgG isotypes (Kim et al., 1994a; Table I), and analyses of human IgG1 molecules (or Fc fragments) and mutated variants indicate that similar IgG residues are involved in binding to FcRn in humans (Kim et al., 1999; Shields et al., 2001). The mapping of the FcRn interaction site on IgG by site directed mutagenesis is also consistent with the high resolution X-ray crystallographic structure of rat FcRn complexed with rat Fc (IgG2a), which demonstrated that residues 252, 253, 254, 288, 307, 309, 310,311, 314, 348, 433, 434, 435, 436 and 439 of IgG make contact to varying extents with FcRn (including carbohydrate contacts of FcRn on Fc) (Martin et al., 2001).

The involvement of His310, His435 and His436 (Tyr in human IgG1) of the IgG1 molecule in interacting with FcRn explains, in part at least, the pH dependence of the FcRn-Fc interaction (Kim et al., 1994b; Raghavan et al., 1995). Despite similarities of the FcRn interaction sites on IgGs across species, recent studies have shown that human and mouse FcRn can show differences in binding specificity (Ober et al., 2001). Site directed mutagenesis has recently been used to determine the molecular basis for this (Zhou et al., 2003; 2005).

The region of the Fc that is involved in binding to FcRn (Kim et al., 1994a; Medesan et al., 1997; Martin et al., 2001) is distinct from the sites involved in binding FcγRI, RII and RIII receptors (the "classical" FcRs), as these recognize sequences primarily located in the lower hinge region (Duncan et al., 1988; Lund et al., 1992; Sarmay et al., 1992; Jefferis et al., 1990; Canfield and Morrison, 1991; Wawrzynczak et al., 1992). In addition, the FcRn interaction site is distinct from the complement factor C1q binding site (Glu318, Lys320 and Lys322) (Wawrzynczak et al., 1992; Duncan and Winter, 1988). Thus, mutation of the FcRn interaction site should neither affect complement fixation nor binding to FcγRI, RII and RIII.

TABLE I

Sequences of Murine and Human IgGs in the Vicinity of the FcRn Interaction Site

|  | 252-254 | 308-312 | 433-436** |
|---|---|---|---|
| mIgG1* | T<u>I</u>T | IM<u>H</u>QD | <u>HNHH</u> |
| mIgG2a | MIS | IQHQD | HNHH |
| mIgG2b | MIS | IQHQD | KNYY |
| mIgG3 | MIS | IQHQD | HNHH |
| hIgG1+ | M<u>I</u>S | VL<u>H</u>QD | HN<u>HY</u> |
| hIgG2 | MIS | VVHQD | HNHY |
| hIgG3 | *MIS* | *VLHQD* | *HNRF* |
| hIgG4 | MIS | VLHQD | HNHY |

*mIgG1 = murine IgG1,
+hIgG + human IgG1
**Simultaneous mutation of His433 and Asn434 had an effect, but as single mutations, His433 to Ala433 and Asn434 to Ala434, no effect was observed (Medesan et al., 1997). Residues of murine IgG1 or human IgG1 that were mutated and found to affect clearance rates in mice (Kim et al., 1994a; Kim et al., 1999) are underlined.

6. Sequence Differences at the Interaction Site on the CH3 Domain of IgG

Of the IgG residues shown in Table I that are involved in binding to FcRn, the most marked differences are in the CH3 domain. This allows sequence differences to be correlated with possible functional differences. For example, murine IgG2b has been shown to have a more rapid clearance rate than IgG1, IgG2a and IgG3 (Pollock et al., 1990). Analysis of sequence differences for the residues at the CH2-CH3 domain interface that have been shown to be important in building the FcRn interaction site indicate that in murine IgG2b, His433, His435, His436 of murine IgG1, IgG2a and IgG3 are replaced by Lys433, Tyr435 and Tyr436 (Table I). These sequence differences provide an ideal system to analyze the role of position 433, 435 and 436 in controlling serum half life and IgG transport. The conversion of lysine 433 to His 433, tyrosine (tyr) 435 to his 435 and tyr 436 to his 436 in an IgG2b molecule results in a mutated IgG2b that has the same in vivo half-life as murine IgG1. U.S. Pat. No. 6,277,375. However, comparative binding studies of mouse IgG1 and mouse IgG2b indicate that these sequence differences result in a loss of pH dependence of the corresponding FcRn-IgG interaction, rather than a reduced affinity (Raghavan et al., 1995; Zhou et al., 2003). This, together with studies of Dall'Acqua et al (2002), indicate that reduced pH dependence can result in decreased serum persistence, most likely due to inefficient release of IgG molecules from cell associated FcRn during exocytosis (Ober et al., 2004a).

Individual mutation of His433 to Ala and Asn434 to Ala/Gln has no effect on binding to FcRn, serum half life or transcytosis U.S. Pat. No. 6,277,375 (Medesan et al., 1997), although His433 and Asn434 have been shown to contact carbohydrate on FcRn in the rat FcRn-Fc complex structure (Martin et al., 2001). In earlier studies (Kim et al., 1994a; 1994c), it was noted that double mutation of His433, Asn434 of mouse IgG1 did have a moderate effect on FcRn-mediated functions in mice. This variation is most likely due to the perturbation of adjacent critical residues such as His435 by the double mutation (whereas single mutations are less perturbing) rather than central involvement of 433 and 434 in the FcRn-IgG (or Fc) interaction. These residues are therefore in proximity to residues that are essential for FcRn-IgG interactions, and are good potential targets for affinity improvement (using a similar strategy to that described in Ghetie et al. (1997) when IgG residues flanking the key residue 253 were targeted for mutagenesis).

In accordance with the present invention, the particular combination of Lys433, Phe434 and Tyr436 (mutant/mutant/wild-type) provides for a ~6-fold increase in human FcRn binding to human IgG1 over wild-type, while retaining pH-dependency of binding to that receptor, improved placental transport, and presumably improved serum half-life. Addition of further mutations Tyr252, Thr254, and Glu256 that flank the central residue Ile253 substantially reduces the pH-dependence of binding to human FcRn, and increases the affinity for this receptor ~30-fold over wild-type.

7. Engineered Antibody Domains with Extended in Vivo Half Lives

Much interest has recently been directed towards modulating the properties (pharmacokinetics, distribution, etc.) of antibodies by site-directed mutagenesis by altering the strength of the FcRn-IgG interaction (Ghetie et al., 1997; Shields et al., 2001; Dall'Acqua et al., 2002; Hinton et al., 2004). The IgG residues involved in building the FcRn interaction site in both rodent and human IgG1 have been identified (Table I and Section 5 above). This data does not rule out the involvement of additional residues of the Fc fragment in regulating IgG levels and FcRn-mediated transport, but it does provide a clear means by which the biological half-life, transport etc. of an antibody or antibody-based molecule or conjugate may be shortened. It also provides a means by which the longevity of a particular antibody may be increased if desired, by re-inserting residues such as Ile253, His310, His435 and His436, should any such residues be found to be mutated in a particular antibody, e.g., IgG2b. Importantly, random mutagenesis of residues flanking these key amino acids, followed by selection, may yield an Fc fragment with increased serum half life (U.S. Pat. No. 6,277,375; Ghetie et al., 1997; Hinton et al., 2004).

In accordance with the present invention, it has surprisingly been found that a particular combination of mutations provide human IgG1 molecules with unique properties. When His433 is changed to Lys, and Asn434 is changed to Phe, but Tyr436 is retained, the human IgG1 molecule show a ~6-fold higher binding affinity for human FcRn relative to wild-type. Importantly, it retains pH-dependent binding to FcRn. Using an ex vivo placental transport model, it shows increased transport across the placental barrier, and is predicted to have improved serum persistence. It would also be expected to be transported more efficiently across cells that express FcRn, such as bronchial or intestinal epithelia (Spiekerman et al., 2002; Dickinson et al., 1999; Yoshida et al., 2004). The claimed invention is broadly applicable to an almost unlimited number of therapeutic uses for the treatment of diseases or disorders, including but not limited to treatment of infectious diseases, autoimmunity, cancer and transplant rejection.

8. Engineering Antibody Molecules with FcRn Blocking Function

As described above, FcRn salvages IgG molecules from degradation and transports these molecules within and across cells. Blocking of FcRn binding to IgGs might therefore be desirable in situations where pathogenic antibodies (e.g., autoreactive) are present, or where an antibody is being used to clear a toxic drug or toxin from the body. Addition of further mutations Met252Tyr, Ser254Thr, and Thr256Glu to the His433Lys, Asn434Phe mutations in human IgG1 substantially reduce the pH-dependence for human FcRn binding, with an approximately 30-fold increased affinity relative to the wild-type antibody. This antibody can block FcRn function in mice and increase clearance rates of IgG. Such FcRn blocking antibodies have a large number of therapeutic uses for the treatment of disease or disorders, including but not limited to the treatment of autoimmunity or blockade of the transfer of pathogenic (autoreactive) antibodies from mother to young.

9. Mutagenesis

In accordance with the present invention, the mutagenesis of IgG constant region genes can be performed using site-specific or site-directed mutagenesis. Site-specific mutagenesis is a technique useful in the preparation of individual proteins or peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique can employ a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, using the PCR™, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Alternatively, PCR™ directed mutagenesis of double-stranded DNA can be used. Such mutants may be readily prepared by, for example, directly synthesizing the Fc fragment by application of nucleic acid reproduction technology, such as the PCR™ technology of U.S. Pat. No. 4,603,102 (incorporated herein by reference).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

10. Therapeutics

The following examples are intended to illustrate the practice of the present invention and are not intended to be limiting. As the invention is demonstrated with a variety of immunoglobulin-like domains, including human IgG1 or Fc-hinge, Fc, CH2-hinge and CH3 domains derived from human IgG1; and mutated antibodies (or fragments) with increased in vivo persistence; and mutated molecules with increased transport across cellular barriers; and mutated molecules with the ability to block FcRn function; it will be understood that other proteins or peptides will be adaptable to similar constructs as those described herein. Likewise, a variety of tags, linker sequences and leader sequences may be employed depending on the particular purification or isolation methods desired to obtain the polypeptide products.

A. Passive Immunotherapy

The protection of humans against infectious agents by passive immunotherapy is attractive, as it provides immediate protection. In contrast, active vaccination requires around 7-10 days for protective antibodies to be elicited. However, a major limitation of passive immunization is that protection is relatively short lived, due to clearance of protective antibodies from the circulation. Protective anti-pathogen antibodies that are longer lived in the circulation would therefore be attractive, and this invention relates directly to this application. Such antibodies would be uses in both therapy of infected individuals, as well as in prophylaxis in the case of likely exposure to an infectious agent.

In addition, infection of the newborn is of particular concern. The passive delivery of protective antibodies that occurs during the third trimester across the maternal-fetal barrier to the fetus could be utilized as a route to deliver protective antibodies, but the efficiency of transport is limited by competition by maternal IgGs (that may not be protective against the specific pathogen). This invention offers a way of increasing the competitive advantage of a therapeutic antibody over the endogenous, maternal antibodies in crossing the placenta.

Possible pathogens that might be targeted include, but are not limited to, *Bacillus anthracis*, West Nile virus, cytomegalovirus and respiratory syncytial virus.

In contrast to increasing serum half lives of antibodies, an additional aspect of this invention is the induction of rapid clearance of antibodies from the body by blocking FcRn function. Exposure to toxins such as snake venom can be treated with anti-venom antibodies. Similarly, overdoses with drugs such as digoxin are currently treated with anti-digoxin Fab fragments (DigiFab™). Following delivery of the antibody and complex formation with the toxin or drug, it might be desirable to induce rapid clearance of antibody-toxin complexes from the body. The current invention describes a modality of inducing rapid clearance of such complexes, by generating antibodies that, through their Fc region, bind tightly and with less pH dependence to FcRn.

B. Disease States

A number of disease states can results in the production of excessive or aberrant (i.e., pathologic) immunoglobulins. The present invention may, in one embodiment, be used to treat such diseases.

Systemic lupus erythematosus (SLE). SLE is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable (Reviewed by Kotzin and O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996). More recently, treatment with rituximab (anti-CD20; a B cell marker) has been attempted.

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (Tsao and Hahn, 1994; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

The mechanisms by which autoantibodies are induced in these autoimmune diseases remains unclear. As there has been no known cause of SLE, to which diagnosis and/or treatment could be directed, treatment has been directed to suppressing immune responses, for example with macrolide antibiotics, rather than to an underlying cause. (e.g., U.S. Pat. No. 4,843,092).

Rheumatoid Arthritis (RA). The exact etiology of RA remains unknown, but the first signs of joint disease appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumour necrosis factor (TNF-$\alpha$), which plays a role in inflammation (Dinarello, 1998; Arend and Dayer, 1995; van den Berg, 2001). The anti-TNF$\alpha$ antibody Remicade™ has been shown to have efficacy in the treatment of RA (Vilcek and Feldmann, 2004).

Sjögren's Syndrome. Sjögren's syndrome is a systemic autoimmune disease in which the body's immune system mistakenly attacks its own moisture producing glands. Sjögren's is one of the most prevalent autoimmune disorders, striking as many as 4,000,000 Americans, with 90% of patients being women. The average age of onset is late 40's although Sjögren's occurs in all age groups in both women and men.

About 50% of the time Sjögren's syndrome occurs alone, and 50% of the time it occurs in the presence of another connective tissue disease. The four most common diagnoses that co-exsist with Sjögren's syndrome are Rheumatoid Arthritis, Systemic Lupus, Systemic Sclerosis (scleroderma) and Polymyositis/Dermatomyositis. Sometimes researchers refer to these situations as "Secondary Sjögren's."

Graft Rejection. Tissue and organ grafts, though powerful tools for treating disease and injury, provoke powerful immune responses that can result in rapid graft rejection in the absence of immunosuppressive therapy. Pioneering studies conducted in the '40s and '50s established that allograft rejection was due to immune responses, later linked to T-lymphocytes. Specific immunological effector mechanisms responsible for graft rejection include cytotoxic T-cells, delayed-type hypersensitivity and antibody-dependent effects. Several therapeutic antibodies that target the T cell marker CD25 have been developed for the treatment of transplant rejection (e.g., Zenapax™, Simulect™). In addition, antibodies of the IgG classes can be involved in transplant rejection (Jordan, S. C. et al., 2005, Pediatric Transplantation, 9, 408-415). Inhibition of FcRn might therefore be used to lower the levels of such deleterious antibodies during transplantation.

Grave's Disease. Marked by nervousness and overstimulation, Grave's disease is the result of an overactive thyroid gland (hyperthyroidism) due to production of autoreactive antibodies that recognize the thyroid stimulating hormone receptor. Thyroid hormones regulate metabolism and body temperature, and are essential for normal growth and fertility. But in excessive amounts, they can lead to the burn-out seen in this relatively common form of thyroid disease. It is unclear what triggers this problem, but the immune system is involved. In Grave's disease patients, they find antibodies specifically designed to stimulate the thyroid.

In many cases, drugs that reduce thyroid output are sufficient to control the condition. A short course of treatment with radioactive iodine, which dramatically reduces the activity of the thyroid, is another option for people past their childbearing years. In some cases, surgery to remove all or part of the thyroid (thyroidectomy) is needed. Surgery can also relieve some of the symptoms of Grave's disease. Bulging eyes, for example, can be corrected by creating enough extra space in the nearby sinus cavity to allow the eye to settle into a more normal position.

Myasthenia Gravis. The number of myasthenia gravis patients in the United States alone is estimated at 0.014% of the population, or approximately 36,000 cases; however, myasthenia gravis is likely under diagnosed. Myasthenia gravis is caused by autoreactive antibodies that recognize the acetylcholine receptor. Previously, women appeared to be more often affected than men, with the most common age at onset being the second and third decades in women, and the seventh and eighth decades in men. As the population ages, the average age at onset has increased correspondingly, and now males are more often affected than females, and the onset of symptoms is usually after age 50.

In acquired myasthenia gravis, post-synaptic muscle membranes are distorted and simplified, having lost their normal folded shape. The concentration of ACh receptors on the muscle end-plate membrane is reduced, and antibodies are attached to the membrane. ACh is released normally, but its effect on the post-synaptic membrane is reduced. The post-junctional membrane is less sensitive to applied ACh, and the probability that any nerve impulse will cause a muscle action potential is reduced.

Cancer. The use of engineered antibodies to target cancers is an area of rapid expansion (Hudson and Souriau, 2003). Multiple antibodies for the treatment of various cancers have to date been approved by the FDA, e.g., Non-Hodgkin's lymphoma (anti-CD20; Rituxan™, Zevalin™), metastatic breast cnacer (anti-Her-2; Herceptin™), acute myeloid leukemia (anti-CD33; Mylotarg™), chronic lymphocytic leukemia (anti-CD52; Campath™) and colon cancer (anti-VEGF: Avastin™). Such antibodies would benefit from having an increased persistence in vivo, as this would result in the need for lower doses at less frequent intervals.

Imaging of tumors with radiolabeled antibodies is also becoming increasingly common. The possibility of inducing the rapid clearance of an imaging agent from the body following imaging would be attractive as it would result in reduced radioactive burden.

11. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials & Methods

Figure 1:
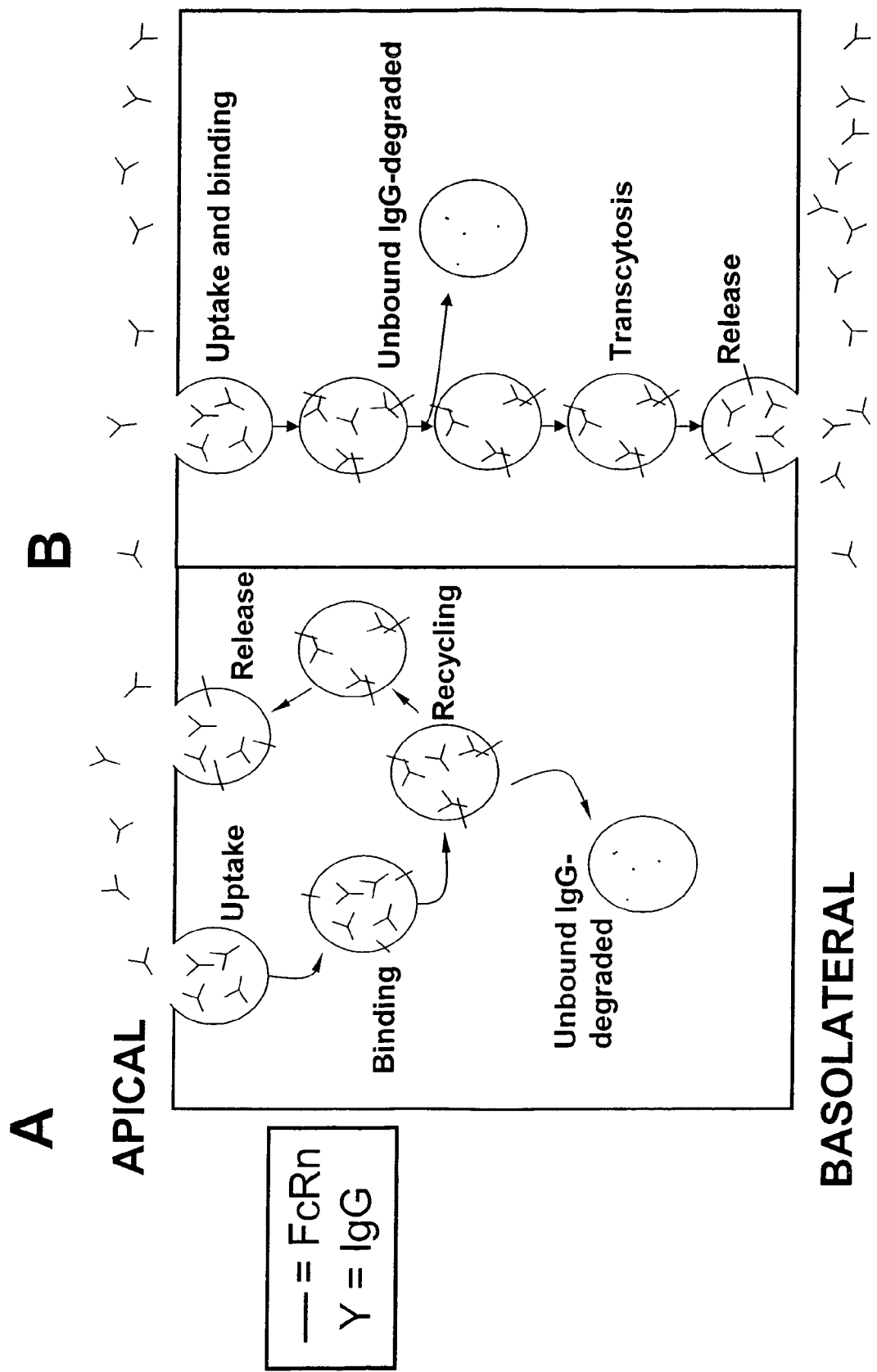
FIGS. 1A-B—Simplified representation of proposed models for trafficking of FcRn in polarized cells.
Figure 2:
FIG. 2—Plasmid map of the vector used to express the recombinant human IgG1 heavy chains. The vectors for expression of mutated heavy chains were generated by cloning mutated heavy chain constant region cassettes as BglII fragments into the BamHI site of a vector containing the anti-lysozyme VH domain (VH36) and leader peptide (LP)

Site directed mutagenesis. The human IgG1 constant regions were mutated using the PCR with mutagenic oligonucleotides and splicing by overlap extension (Horton et al., 1989). Restriction sites encompassing the mutated sequence in the constant region gene were used for recloning the mutated regions as smaller subfragments of the entire constant region gene. Following recloning, constant region genes were sequenced to ensure insertion of the desired mutation without second site mutations. Mutated genes were recloned into the final expression construct (FIG. 2) using standard methods of molecular biology.

Transfection for expression of antibodies. NSO cells expressing a human anti-lysozyme specific light chain (Hu-Lys5: Foote and Winter, 1992) were transfected by electroporation with heavy chain expression constructs (FIG. 2) encoding an anti-lysozyme heavy chain with mutations in the Fc region as described. Transfectants were selected in medium containing mycophenolic acid/xanthine (as in Foote and Winter, 1992) and culture supernatants screened for expression of antibody by ELISA. Positive clones were expanded further for protein production.

Expression, purification and labeling of IgGs. Recombinant human IgG s (wild-type and mutated variants: all lysozyme specific) were purified from culture supernatants using lysozyme-Sepharose as described in Foote and Winter (1992). Human IgG1 was radiolabeled with Iodogen as described in Kim et al. (1994a).

Expression and purification of recombinant FcRn. Recombinant, soluble human FcRn was expressed in High-Five cells ((Invitrogen) infected with recombinant baculoviruses and protein purified using $Ni^{2+}$-NTA-agarose followed by HPLC using a HiLoad 26/60 Superdex™ 200 prep grade column (Pharmacia) as described (Zhou et al., 2003).

Surface plasmon resonance analyses. Binding of human FcRn to immobilized IgGs was carried out as described previously (Zhou et al., 2005). FcRn binds to two sites on IgG that are not equivalent (Zhou et al., 2005). Data were therefore fitted to a two site model involving two independent binding sites. This generated estimates for two dissociation constants ($K_{D1}$ and $K_{D2}$), which are taken to represent occupancy of the first site on IgG ($K_{D1}$) followed by occupancy of the second site with lower affinity ($K_{D2}$).

Enzyme linked immunosorbent assays. To determine total serum IgG levels in Swiss mice, enzyme linked immunosorbent assays (ELISAs) were used. 96-well plates were coated with rabbit anti-mouse IgG (heavy chain specific; Zymed) and then non-specific sites blocked with 2% bovine serum albumin in PBS. Dilutions of serum samples were made in PBS and then added to the wells. Bound mouse IgGs were detected using horse rabbit peroxidase conjugated rabbit anti-mouse IgG (heavy and light chain specific; Zymed). A standard curve was generated using purified mouse IgGs (The Binding Site, U.K.).

Analyzing the effects of mutated human IgG1 molecules on IgG levels in mice. Effects on clearance of radiolabeled human IgG1: Swiss mice were injected intravenously with $^{125}$I labeled wild-type human IgG1 and whole body counting (AtomLab 100 Dose Calibrator) used to assess levels of radiolabeled IgG1. Three days later, mice were injected intravenously with 500 µg of either wild-type human IgG1 or 500 µg or 200 µg mutated human IgG1 containing Tyr252, Thr254, Glu256, Lys433, Phe434 and Tyr436. Levels of radiolabeled human IgG1 were determined at the times indicated in FIG. 4 using whole body counting (AtomLab 100 Dose Calibrator). Effects on endogenous mouse IgG levels: The levels of serum IgGs in Swiss mice were determined by ELISA of diluted serum samples. Mice were injected intravenously with 500 µg wild-type human IgG1 or 500 µg mutated human IgG1 containing Tyr252, Thr254, Glu256, Lys433, Phe434 and Tyr436. Serum levels of endogenous (mouse) IgGs were determined by ELISA at the times indicated on FIG. 5 following injection.

Example 2

Results

Analyses of the interactions of human FcRn with wild-type human IgG1 and human IgG1 mutants containing Lys433, Phe434 and His436 (mutated to corresponding mouse IgG1 residue at position 436) or Lys433, Phe434 and Tyr436 (wild-type residue at position 436) indicates that the mutant with the wild-type Tyr436 has an approximately two-fold higher affinity than the mutant containing His436 (Table I). In addition, both mutants have substantially higher affinities for human FcRn than the corresponding wild-type human IgG1. These affinities are further improved when mutations of Met252 to Tyr, Ser254 to Thr and Thr256 to Glu are added to the position 433, 434 (and 436) mutations. Higher affinity for binding to human FcRn is retained for the human IgG1 variant containing the wild-type residue Tyr, rather than histidine, at position 436 (Table II). Taken together, the data therefore indicate that Tyr436 is preferred over His436 for the interaction of human IgG1 with human FcRn.

The pH dependencies of the interactions of wild-type human IgG1 and mutated human IgG1 variants with Lys433, Phe434 and Tyr436, or Tyr252, Thr254, Glu256, Lys433, Phe434 and Tyr436 with human and mouse FcRn have also been analyzed (FIGS. 3A-F). The data shown in FIGS. 3A, 3B, 3E and 3F indicate that addition of Tyr252, Thr254 and Glu256 to human IgG1 containing Lys433, Phe434 and Tyr436 reduces the pH dependence of the interaction with human FcRn (similar results are observed to binding to mouse FcRn: data not shown). Comparison of FIGS. 3A and 3C also indicates that the interaction of the human IgG1 mutant containing Lys433, Phe434 and Tyr436 with mouse FcRn is less pH-dependent than the corresponding interaction for human FcRn.

The binding analyses therefore show that human IgG1 mutants containing Lys433, Phe434 and Tyr436, or Tyr252, Thr254, Glu256, Lys433, Phe434 and Tyr436 have higher affinity binding for FcRn relative to wild-type human IgG1. In addition, the pH dependence of human IgG1 containing Tyr252, Thr254 and Glu256 for binding to FcRn is reduced relative to IgG1 (mutants) containing wild-type human IgG1 residues at positions 252, 254 and 256.

The ability of the human IgG1 mutant containing Tyr252, Thr254, Glu256, Lys433, Phe434 and Tyr436 to enhance the clearance rates of IgGs in mice has been analyzed. This was first investigated by injecting mice with radiolabeled ($^{125}$I) wild-type human IgG1, and three days later the mice were injected with different doses of human IgG1 mutant containing Tyr252, Thr254, Glu256, Lys433, Phe434 and Tyr436 or wild-type human IgG1. FIG. 4 shows the levels of radioactivity remaining in the mice at different times during the experiment. These levels were assessed using body counting and therefore indicate the whole body, rather than serum, levels of labeled IgG1. Following injection of 500 pg human IgG1 mutant a rapid drop in the levels of radioactive IgG1 in the mice is observed. Similar, but a less marked effect, is observed for mice treated with 200 µg human IgG1 mutant (FIG. 4). In contrast, treatment of mice with 500 µg wild-type human IgG1 has no observable effect on the clearance of the radiolabeled IgG1.

The inventor next analyzed whether injection of the human IgG1 mutant containing Tyr252, Thr254, Glu256, Lys433, Phe434 and Tyr436 resulted in a lowering of endogenous IgGs in the serum of mice. Endogenous (steady state) serum IgG levels were determined and mice were subsequently injected with either 500 µg human IgG1 mutant or wild-type human IgG1. Relative to treatment of mice with wild-type human IgG1, treatment with the human IgG1 mutant resulted in significant decreases in endogenous serum IgG levels that persisted for about 4 days (FIG. 5).

Taken together, the data shown in FIGS. 4-5 indicate that the human IgG1 mutant containing Tyr252, Thr254, Glu256, Lys433, Phe434 and Tyr436 can reduce levels of both exogenous and endogenous IgGs in mice. Further, as the inventor has analyzed the in vivo effects of the human IgG1 mutant on IgG levels in both the serum compartment and whole body, our observations suggest that inhibition of FcRn function acts at diverse sites throughout the body.

TABLE II

Affinities of the Human IgG1 Variants for Binding to Human FcRn

| | $K_D1$ (µM)[1] | $K_D2$ (µM)[1] |
|---|---|---|
| Wild-type human IgG1 | 0.37 | 2.1 |
| H433K/N434F[2] | 0.057 | 0.66 |
| H433K/N434F/Y436H | 0.139 | 1.7 |
| M252Y/S254T/T256E/ H433K/N434F[2] | 0.012 | 0.35 |

TABLE II-continued

Affinities of the Human IgG1 Variants
for Binding to Human FcRn

| | $K_D1$ (µM)[1] | $K_D2$ (µM)[1] |
|---|---|---|
| M252Y/S254T/T256E/<br>H433K/N434F/Y436H | 0.024 | 0.54 |

[1]There are two non-equivalent binding sites on IgG for human FcRn. Data were therefore analyzed using two-site binding model. Affinities of the interactions of human FcRn with immobilized IgGs were determined as in Zhou et al. (2003; 2005), but using a model involving two independent binding sites.
[2]These mutants have the wild-type residue tyrosine at position 436. Nomenclature: H433K = His433 to Lys, etc.

Example 3

Methods & Results

Labeling of antibodies. Antibodies were labeled using Iodogen or biotinylated in 0.1 M carbonate buffer (pH 8.5) using 9 µg EZ-link Sulfo-NHS biotin (Pierce) per milligram of antibody as described (Firan et al., 2001). Prior to use in studies, all labeled antibodies were compared with their unlabeled counterparts using surface plasmon resonance to ensure that labeling had not altered their binding characteristics.

Placental transport assays. Essentially the same methods as those described previously were used (Firan et al., 2001). Three mgs of each of wild-type IgG1 or human IgG1 mutant containing Lys433 and Phe434 with the wild-type residue Tyr at position 436 (labeled with either biotin or $^{125}$I) were added to the maternal compartment of the ex vivo placental model and transport to the fetal compartment analyzed by sample collection at the indicated times. Following collection, samples were centrifuged at 1500 g for 10 minutes and pellets discarded. The amounts of IgG in the supernatant were determined by ELISA (for biotinylated IgG) or by γ-counting after precipitation with 10% TCA.

Results. FIG. 6 shows that the human IgG1-derived mutant, HN (His433→Lys, Asn434→Phe) transports better across the human placenta than wild-type human IgG1.

. . .

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,843,092
U.S. Pat. No. 6,277,375
Antohe et al., *Human Immunol.*, 62:93-105, 2001.
Arend and Dayer, *Arthritis Rheum.*, 38:151-160, 1995.
Bitonti et al., *Proc. Natl. Acad. Sci., USA*, 101:9763-9768, 2004.
Burmeister et al., *Nature*, 336-343, 1994b.
Dall'Acqua et al., *J Immunol.*, 169:5171-5180, 2002.
Dickinson et al., *J. Clin. Invest.*, 104, 903-911, 1999.
Dinarello, *Int. Rev. Immunol.*, 16:457499, 1998.
Edelman et al., *Proc. Natl. Acad. Sci., USA*, 63:78-85, 1969.
Firan et al., *Int. Immunol.*, 13(8):993-1002, 2001.
Foote and Winter, *J. Mol. Biol.*, 224:487-499, 1992.
Ghetie and Ward, *Annu. Ref. Immunol.*, 18:739, 2000.
Ghetie et al., *Eur. J. Immunol.*, 26(3):690-696, 1996.
Ghetie et al., *Immunol Today*, 18(12):592-598, 1997.
Hinton et al., *J. Biol. Chem.*, 279:6213-6216, 2004.
Horton et al., *Gene*, 77:61-68, 1989.
Hudson and Souriau, *Nat. Med.*, 9:129-134, 2003.
Israel et al., *Immunol.*, 89:573-578, 1996.
Israel et al., *J. Immunol.*, 154:6246-6251, 1995.
Junghans and Anderson, *Proc. Natl. Acad. Sci. USA*, 93(11):5512-5516, 1996.
Kabat et al., In: *Sequences of proteins of immunological interest*, U.S. Department of Health and Human Services, 1991.
Kacskovics et al., *J. Immunol.*, 164:1889-1897, 2000.
Kim et al., *Eur. J. Immunol.*, 24:2429-2434, 1994a.
Kim et al., *Eur J. Immunol.*, 24:542-548, 1994b.
Kim et al., *Scand. J. Immunol.*, 40:457-465, 1994c.
Kim et al., *Eur J. Immunol.*, 29:2819-2825, 1999.
Kobayashi et al., *Am. J. Physiol. Renal Physiol.*, 282, F358-F365, 2002.
Kotzin and O'Dell, In: *Samler's Immunologic Diseases*, 5th Ed., Frank et al. (Eds.), Little Brown & Co., Boston, 667-697, 1995.
Kotzin, *Cell*, 85:303-306, 1996.
Kristoffersen and Matre, *Eur J. Immunol.*, 26(7):1668-1671, 1996.
Leach et al., *J. Immunol.*, 157:3317-3322, 1996.
Lipsky, In: *Harrison's principles of internal medicine*, Fauci et al.(Eds.), 14th Ed., NY, McGraw-Hill, 1880-1888, 1998.
Martin et al., *Mol. Cell*, 7:867-877, 2001.
Martin et al., *Molecular Cell.*, 7:867-877, 2001.
McCarthy et al., *J. Cell Sci.*, 113:1277-1285,2000.
Medesan et al., *Eur. J. Immunol.*, 26:2533-2536, 1996.
Medesan et al., *J. Immunol.*, 158(5):2211-2217, 1997.
Ober et al., *Int. Immunol.*, 13:1551-1559, 2001.
Ober et al., *J. Immunol.*, 172:2021-2029, 2004.
Ober et al., *J. Immunol.*,.172(4):2021-2029, 2004.
Ober et al., *Proc. Natl. Acad. Sci. USA*, 101 (30):11076-11081, 2004.
Ober et al., *Proc. Natl. Acad. Sci., USA*, 101: 11076-11081, 2004.
Ohnishi et al., *Nephrol. Dial. Transplant.*, 9:1747-1750, 1994.
Popov et al., *Mol. Immol.*, 33:521, 1996.
Raghavan et al., *Biochemistry*, 34:14649, 1995.
Roberts et al., *J. Cell Biol.*, 1 11: 1867-1876, 1990.
Rodewald and Kraehenbuhl, *J. Cell Biol.*, 99:S159-S164, 1984.
Shields et al., *J. Biol. Chem.*, 276:6591-6604, 2001.
Simister etal., *Eur. J. Immunol.*, 26(7):1527-1531, 1996.
Simister, *Vaccine*, 21:3365-3369, 2003.
Spiekermann et al., *J. Exp. Med.*, 196(3):303-310, 2002.
Story et al., *J. Exp. Med.*, 180:2377-2381, 1994.
Tsao and Hahn, *Int Rev Immunol.*, 1 1(4):305-320, 1994.
Vaccaro et al., *Nat. Biotech.*, 23, 1283-1288, 2005.

van den Berg, *Semin. Arthritis Rheum.*, 30(5S-2):7-16, 2001.

Vilček and Feldmann, *Trends in Pharmacological Sciences*, 25:201-209, 2004.

Wallace and Rees, *Biochem. J.*, 188:9-16, 1980.

Yoshida et al., *Immunity*, 20:769-783, 2004.

Zhou et al., *J. Mol. Biol.*, 332:901-913, 2003.

Zhou et al., *J. Mol. Biol.*, 345, 1071-1081, 2005.

What is claimed is:

1. An IgG molecule comprising a human Fc domain wherein (EU numbering) His433 is changed to Lys433, Asn434 is changed to Phe434, and Tyr436 is unchanged.

2. The IgG molecule of claim 1, wherein the IgG molecule is an IgG1 molecule.

3. The IgG molecule of claim 1, wherein the IgG molecule Fc domain contains wild-type residues at positions 252, 254 and 256.

4. The IgG molecule of claim 1, wherein the IgG molecule Fc domain contains wild-type residues at all positions other than 433 and 434.

* * * * *

UNITED STATES PATENT AND TRADEMARK OFFICE
CERTIFICATE OF CORRECTION

| | | |
|---|---|---|
| PATENT NO. | : 8,163,881 B2 | |
| APPLICATION NO. | : 11/445475 | |
| DATED | : April 24, 2012 | |
| INVENTOR(S) | : E. Sally Ward Ober | |

It is certified that error appears in the above-identified patent and that said Letters Patent is hereby corrected as shown below:

In title page, item (56) References Cited - OTHER PUBLICATIONS, insert
--Antohe *et al.*, "Expression of functionally active FcRn and the differentiated bidirectional transport of IgG in human placental endothelial cells," *Human Immunol.*, 62:93-105, 2001.--.

Signed and Sealed this
Twenty-sixth Day of June, 2012

David J. Kappos
*Director of the United States Patent and Trademark Office*